(12) United States Patent
Fritz et al.

(10) Patent No.: US 11,130,722 B2
(45) Date of Patent: Sep. 28, 2021

(54) METHOD AND PLANT FOR PRODUCING ETHYLENE (71) Applicant: LINDE AKTIENGESELLSCHAFT, Munich (DE)

(72) Inventors: Helmut Fritz, Munich (DE); Andreas Obermeier, Egmating (DE); Andreas Peschel, Wolfratshausen (DE); Tuat Pham Duc, Penzberg (DE); Desislava Tota, Munich (DE)

(73) Assignee: LINDE AKTIENGESELLSCHAFT, Munich (DE)

( * ) Notice: Subject to any disclaimer, the term of this patent is extended or adjusted under 35 U.S.C. 154(b) by 0 days.

(21) Appl. No.: 16/646,964

(22) PCT Filed: Sep. 13, 2018

(86) PCT No.: PCT/EP2018/074733
§ 371 (c)(1),
(2) Date: Mar. 12, 2020

(87) PCT Pub. No.: WO2019/053122
PCT Pub. Date: Mar. 21, 2019

(65) Prior Publication Data
US 2020/0207686 A1    Jul. 2, 2020

(30) Foreign Application Priority Data
Sep. 13, 2017   (EP) .................................. 17190901

(51) Int. Cl.
*C07C 5/48*    (2006.01)
*C07C 7/09*    (2006.01)
(Continued)

(52) U.S. Cl.
CPC .................. *C07C 5/48* (2013.01); *C07C 7/09* (2013.01); *C07C 7/12* (2013.01); *C07C 11/04* (2013.01)

(58) Field of Classification Search
CPC .. C07C 5/48; C07C 7/12; C07C 11/04; C07C 7/09
See application file for complete search history.

(56) References Cited

U.S. PATENT DOCUMENTS 5,457,256 A * 10/1995 Mitariten ................ C07C 5/333
585/655
5,744,687 A * 4/1998 Ramachandran .... C10G 70/046
585/829

(Continued)

FOREIGN PATENT DOCUMENTS

DE    3813976 A1    11/1989
DE    275452 A1    1/1990
(Continued)

OTHER PUBLICATIONS

Eurasian Patent Application No. 202090482, Office Action dated Dec. 11, 2020, with English translation, 4 pages.
(Continued)

*Primary Examiner* — Youngsul Jeong
(74) *Attorney, Agent, or Firm* — Lathrop GPM LLP (57) ABSTRACT

Proposed is a process for producing ethylene wherein using a dehydrogenation of ethane a process gas containing at least ethane, ethylene and compounds having a lower boiling point than ethane and ethylene is formed, wherein using at least a part of the process gas a separation input is formed and subjected to a low-temperature separation (6) in which the separation input is cooled and in which one or more condensates are separated from the separation input, wherein the condensate(s) are at least partly subjected to a low-temperature rectification to obtain a gaseous first frac-
(Continued)

tion and a liquid second fraction, wherein the gaseous first fraction contains at least the ethane and the ethylene in a lower proportion than in the separation input and the compounds having a lower boiling point than ethane and ethylene in a higher proportion than in the separation input. It is provided that the first fraction is at least partly subjected to a pressure swing adsorption (7) by means of which a third fraction containing predominantly or exclusively ethylene and ethane and a fourth fraction containing predominantly or exclusively methane and carbon monoxide are formed. A corresponding plant (100) likewise forms part of the subject matter of the present invention.

13 Claims, 2 Drawing Sheets

(51) Int. Cl.
*C07C 7/12* (2006.01)
*C07C 11/04* (2006.01)

(56) References Cited

U.S. PATENT DOCUMENTS 9,776,935 B2 * 10/2017 Palo .................. B01D 53/22
2017/0113983 A1 * 4/2017 Mitkidis ............... C07C 11/04

FOREIGN PATENT DOCUMENTS

| DE | 102008060783 A | 6/2010 |
| EP | 0816290 A1 | 1/1998 |
| EP | 1024187 A1 | 8/2000 |
| EP | 3278860 A1 | 2/2018 |

OTHER PUBLICATIONS

PCT/EP2018/074733 International Search Report and Written Opinion dated Nov. 13, 2018, 10 pages.

* cited by examiner

METHOD AND PLANT FOR PRODUCING ETHYLENE

The invention relates to a process for producing ethylene and a corresponding plant according to the preambles of the independent claims.

PRIOR ART

Oxidative dehydrogenation (ODH) of paraffins having two to four carbon atoms is known in principle. In ODH the recited paraffins are reacted with oxygen to afford inter alia olefins of identical carbon number and water.

ODH may be advantageous compared to established processes for producing olefins such as steamcracking or catalytic dehydrogenation. For instance, there is no thermodynamic equilibrium limitation on account of the exothermicity of the reactions involved. ODH may be performed at comparatively low reaction temperatures.

Regeneration of the employed catalysts is in principle not necessary since the presence of oxygen allows an in situ regeneration. Finally, compared to steamcracking, smaller amounts of worthless by-products such as coke are formed.

For further details concerning ODH, reference is made to the relevant technical literature, for example Ivars, F. and López Nieto, J. M., Light Alkanes Oxidation: Targets Reached and Current Challenges, in: Duprez, D. and Cavani, F. (ed.), Handbook of Advanced Methods and Processes in Oxidation Catalysis: From Laboratory to Industry, London 2014: Imperial College Press, pages 767 to 834, or Gärtner, C. A. et al., Oxidative Dehydrogenation of Ethane: Common Principles and Mechanistic Aspects, ChemCatChem, vol. 5, no. 11, 2013, pages 3196 to 3217.

The invention is hereinbelow described in particular having regard to ODH of ethane (so-called ODH-E). In addition to the oxidative dehydrogenation of ethane a non-oxidative dehydrogenation of ethane for producing ethylene may, however, also be effected in principle. The present invention is suitable for such a process too.

In addition to the primary products ethylene and water at higher conversions in ODH, in particular ODH-E, appreciable amounts of carbon monoxide and carbon dioxide and possibly acetic acid are formed as by-products. Depending on the reaction conditions residual oxygen may also be present in a corresponding process gas, i.e. a gas mixture withdrawn from the reactor. Methane may likewise be formed as a by-product or already be present in the input into the reactor and traverse the reactor essentially unaffected as a component exhibiting inert behaviour. The recited components must be removed from the process gas in downstream separation steps.

As is also elucidated hereinbelow, particularly due to the low contents of methane in an ODH-E process gas, if present at all, it is not readily possible to employ known separating processes and separating devices used for separation of process gases from steamcrackers for example for corresponding process gases from ODH-E without accepting product and reactant losses. This applies in particular to a separation step in which ethane and ethylene and higher boiling components if present in the process gas are removed from lower boiling components. This step corresponds in principle to a so-called demethanization in a separation of a process gas from a steamcracker.

The problem addressed by the present invention is that of improving corresponding processes and plants and addressing the recited problems in a corresponding separation, in particular for a process gas from ODH-E.

DISCLOSURE OF THE INVENTION

Against this background, the present invention proposes a process for producing ethylene, in particular by the elucidated oxidative dehydrogenation, in particular of ethane, and a corresponding plant having the features of the independent claims. Embodiments are in each case provided by the dependent claims and the description which follows.

Material streams, gas mixtures etc. may in the context of the present linguistic usage contain "predominantly" one or more components, wherein this indication may represent a content of at least 90%, 95%, 99%, 99.5%, 99.9% or 99.99% on a molar, weight or volume basis. If a plurality of components are reported the indication "predominantly" relates to the sum of all components. If reference is made for example to "oxygen", "methane" or "ethylene" a pure gas or else a mixture rich in these respective components may be concerned.

Material streams, gas mixtures etc. may in the context of the present linguistic usage also be "enriched" or "depleted" in one or more components, wherein these terms are based on a content in a starting mixture. They are "enriched" when they contain not less than 1.5 times, 2 times, 5 times, 10 times, 100 times or 1000 times the content, and "depleted" when they contain not more than 0.75 times, 0.5 times, 0.1 times, 0.01 times or 0.001 times the content, of one or more components based on the starting mixture.

The terms "pressure level" and "temperature level" are used hereinbelow to characterize pressures and temperatures, these being intended to express that pressures and temperatures need not be present in the form of exact pressure/temperature values. A pressure level or temperature level may for example be within ±1%, 5%, 10% or 20% of a mean value. A plurality of pressure and temperature levels may represent disjoint or overlapping ranges. The same pressure/temperature level may for example still be present even when pressures and temperatures have been reduced on account of transmission losses or cooling. Pressure levels reported here in bar are absolute pressures.

A "rectification column" in the context of the present linguistic usage is a separation unit set up for at least partial fractionation of a substance mixture fed in in gaseous or liquid form or in the form of a biphasic mixture having liquid and gaseous components, possibly even in the supercritical state, by rectification, i.e. to respectively produce pure substances or at least substance mixtures of different composition from the substance mixture. Rectification columns are typically configured as cylindrical metal containers provided with internals, for example separating trays or ordered or unordered packings. A rectification column comprises a bottoms evaporator. This is a device having a heat exchanger which is heated and adapted for heating a liquid fraction accumulating in the bottom of the rectification column, also known as bottoms liquid. By means of a bottoms evaporator a part of the bottoms product is continuously evaporated and recycled in gaseous form into the rectification column.

The present invention relates to separating processes and corresponding separating devices similar in terms of the underlying concept, but not the implementation realized according to the invention, to separating processes and separating devices known for other process gases, for example from steamcrackers. Such separating processes and separating devices are described for example in the article "Ethylene" in Ullmann's Encyclopedia of Industrial Chemistry, Online Edition, 15 Apr. 2007, DOI 10.1002/14356007.a10_045.pub2. An essential step in such separating processes is often so-called demethanization in which from the process gas, optionally after removal of further components, methane and compounds lower boiling than methane are removed from higher boiling components. For details of known demethanization processes reference is made to the cited specialist literature.

Advantages of the Invention

As mentioned at the outset a typical process gas formed by ODH-E contains not only primary products such as ethylene (and possibly acetic acid) but also inter alia unconverted ethane, carbon monoxide and carbon dioxide and possibly oxygen and methane. The process gas typically also contains water and possibly small amounts of inert gases, wherein "inert gases" is to be understood as meaning generally gases which react only in small proportions, if at all, in ODH and not only the classical inert gases such as nitrogen or noble gases. Methane too exhibits essentially inert behaviour in ODH-E.

The same applies in similar fashion to process gases from other processes for producing ethylene, for example (non-oxidative) dehydrogenation of ethane, wherein hereinbelow, as repeatedly mentioned, for the sake of simplicity reference is made to ODH-E. A separation arranged downstream must remove the recited by-products from the desired primary product(s) and the unconverted ethane and the inert gases.

Separation is typically effected, as also illustrated with reference to the accompanying FIG. 1, after a cooling and condensation of the process gas, a removal of carbon dioxide, a compression and a drying. The process gas still containing after the recited steps essentially ethylene, unconverted ethane, oxygen, carbon monoxide, possibly methane and relatively small amounts of other components is subjected to a low-temperature separation in which for example a staged condensation of the process gas is effected. The remaining gas fractions are in each case supplied to the next condensation step. The condensates are conventionally subjected to a low temperature rectification to form a gas fraction and a liquid fraction. The gas fraction from the low temperature rectification is conventionally combined with the gas fraction remaining downstream of the last condensation step to afford a further gas fraction, the so-called fuel gas fraction/tail gas fraction, and sent to a thermal recovery. The liquid fraction from the low temperature rectification is subjected to further separating steps.

The tail gas fraction shall contain, if present, at least the predominant part of the oxygen, carbon monoxide and methane contained in the process gas supplied to the low-temperature separation. By contrast, ethylene and ethane shall be transferred at least predominantly into the liquid fraction from the low-temperature rectification together with high-boiling compounds if present in the process gas and not previously removed. In principle product losses shall be avoided by transferral of corresponding compounds into the tail gas fraction.

However, the separation efficiency in a classical low temperature rectification as is employed for example for demethanization in steamcracking processes depends essentially on the content of methane in the process gas supplied to the low temperature rectification because a liquid reflux formed essentially from methane is formed. If contents of methane are excessively low the reflux cannot be provided in a sufficient amount, if at all. Thus, excessively low amounts of methane result in excessively high losses of ethylene and unconverted ethane in the tail gas fraction and thus in economic disadvantages compared to other processes.

The present invention solves these problems in a process for producing ethylene wherein using a dehydrogenation of ethane a process gas containing at least ethane, ethylene and compounds having a lower boiling point than ethane and ethylene is formed and wherein using at least a part of the process gas a separation input is formed and subjected to a low-temperature separation in which the separation input is cooled and in which one or more condensates are separated from the separation input. At least the condensate(s), or in embodiments also a residue remaining in gaseous form in such a condensation, are at least partly subjected to a low-temperature rectification to obtain a gaseous first fraction and a liquid second fraction, wherein the gaseous first fraction contains at least the ethane and the ethylene in a lower proportion than in the separation input and the compounds having a lower boiling point than ethane and ethylene in a higher proportion than in the separation input.

While the gaseous first fraction contains at least the ethane and ethylene in a lower proportion than in the separation input, larger or smaller amounts thereof are still present in the gaseous first fraction depending on the embodiment. The invention therefore provides that the gaseous first fraction is at least partly subjected to a pressure swing adsorption by means of which a third fraction containing predominantly or exclusively ethane and ethylene and a fourth fraction containing predominantly or exclusively the compounds having a lower boiling point than ethane and ethylene are formed. Through the use of pressure swing adsorption ethane and ethylene may be recovered and resupplied to the process in simple and efficient fashion. This brings about an enhancement of the overall efficiency of the process since the recovered ethane and ethylene may be materially and not thermally recovered.

The basic idea of the present invention thus consists in a combination of a low-temperature separation with a pressure swing adsorption. Various embodiments may be envisaged in which in each case a cooling of the separation input in the low-temperature separation is undertaken to a certain temperature level so that one or more condensates are separated. These condensates, or as mentioned in certain embodiments also a residue remaining in gaseous form, are at least partly subjected to the low-temperature rectification. The embodiments of the present invention differ in particular, but not only, in terms of the temperature levels to which the cooling of the separation input for the purposes of separation of the condensate(s) is effected and also in terms of the question of whether an introduction of the gaseous residue into the low temperature rectification is undertaken or not. Further details of the recited embodiments and further embodiments are elucidated hereinbelow. A pressure swing adsorption is part of the elucidated embodiments in each case.

A process gas treated in the context of the present invention may in principle contain directly at the outlet of the employed reactor(s) for example up to 40 mole percent of ethane, 5 to 40 mole percent of ethylene, 0 to 10 mole percent of acetic acid, 0 to 3 mole percent of carbon dioxide, 0 to 5 mole percent of carbon monoxide, 5 to 70 mole percent of water, 0 to 5 mole percent of oxygen, 0 to 5 mole percent of methane and 0 to 50 mole percent of nitrogen. Further components may altogether be present in a content of 0 to 3 mole percent. Acetic acid, water and carbon dioxide in particular are removed upstream of the steps proposed according to the invention so that the separation input employed in the context of the present invention contains predominantly or exclusively the other recited components.

The use of comparatively low temperatures allows the content of ethane and ethylene in the gaseous first fraction to be markedly reduced in principle because more ethane and ethylene are transferred into the condensate(s).

When using comparatively low temperatures it is therefore also possible in a first embodiment to process only the condensate(s) in the low temperature rectification because the uncondensed proportion of the separation input contains only small amounts of ethane and ethylene. In this case only the first fraction formed from the condensates by means of the low-temperature rectification may be processed in a pressure swing adsorption. The amount of the gas to be processed in the pressure swing adsorption is therefore comparatively small compared to other embodiments. Details are elucidated in particular with reference to the accompanying FIG. 2.

Figure 3:
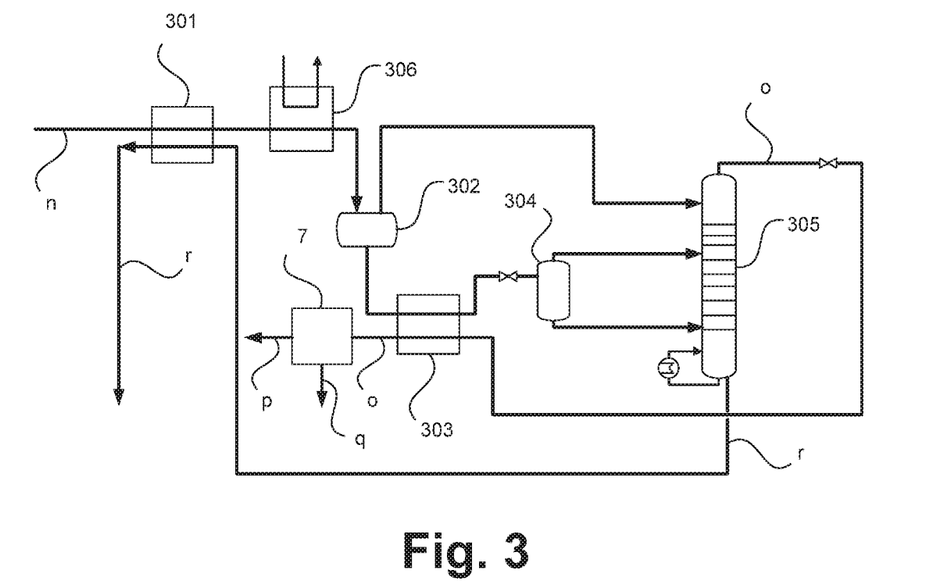
FIG. 3 shows a low-temperature separation for use in a plant according to one embodiment of the invention.

If, by contrast, in a second embodiment the low-temperature separation comprises undertaking a cooling at a similar pressure range as in the first embodiment but at a markedly higher temperature level less ethane and ethylene condense out so that, here too, preferably the uncondensed proportions of the separation input are subjected to the low-temperature rectification, as elucidated in particular with reference to FIG. 3. The content of ethane and ethylene in the first fraction is typically also higher here and is accordingly largely reduced in the subsequent pressure swing adsorption. The pressure swing adsorption may therefore have to process a larger amount of gas compared to when lower temperatures are used.

Figure 4:
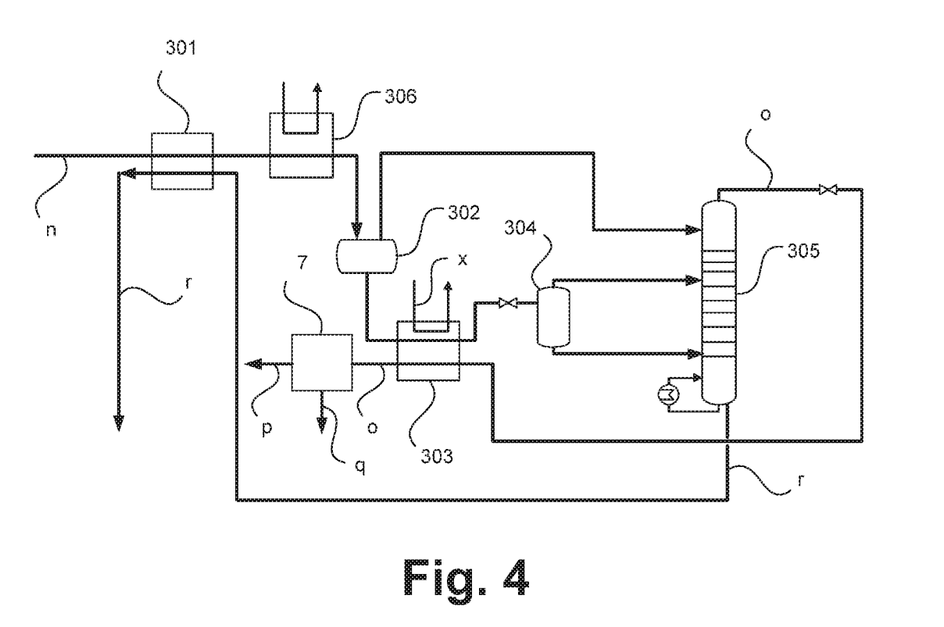
FIG. 4 shows a low-temperature separation for use in a plant according to one embodiment of the invention.

In a third embodiment, as elucidated in particular with reference to FIG. 4, the low-temperature separation advantageously comprises undertaking a cooling of the separation input in one or more cooling steps at a similar temperature range as in the first embodiment but at lower pressure. A proportion of the separation input separated as condensate after the cooling steps is at least partly decompressed and supplied to the low-temperature rectification. The liquid fraction separated by the cooling serves as reflux in the low-temperature rectification.

In each case, i.e. the three elucidated embodiments, the process gas/the separation input may be subjected to a compression upstream of the low-temperature separation, wherein the third fraction containing predominantly or exclusively ethane and ethylene is at least partly combined with the process gas/the separation input and may be subjected to the compression together with the process gas/the separation input. Details of the pressure levels achieved during the compression in different embodiments are elucidated below. In this way ethane and ethylene may be resupplied to the low-temperature separation and thus in particular in the liquid second fraction downstream of the elucidated low-temperature rectification may be supplied to a further low-temperature rectification for separation of ethane and ethylene, i.e. a so-called splitter. The thus obtained ethylene may be discharged as product while by contrast the ethane is recycled to the employed reactor(s).

It is in principle also possible in the three embodiments to undertake a heat integration such that the separation input in the low-temperature separation is at least partly cooled by transferral of heat to the gaseous first fraction and/or the liquid second fraction. In this way it is possible to simultaneously bring for example the gaseous first fraction to a temperature suitable for the pressure swing adsorption. Details thereof are also elucidated hereinbelow.

As mentioned, in the first embodiment of the present invention the separation input is cooled to comparatively low temperature levels, for example to a temperature level of −20° C. to −100° C., in particular −60° C. to −100° C., for example −80° C. to −100° C., in the low-temperature separation for separating the condensate(s). In other words the condensates are separated at an appropriate temperature level. Appropriate temperature levels may be achieved for example using C2 refrigerant, in particular ethylene, in a familiar refrigeration circuit. Appropriate low temperatures may also be achieved by decompressing the gaseous first fraction formed in the low-temperature rectification. In this way yet lower temperatures may be achieved, albeit only using correspondingly complex machines. In the context of the invention the use of the pressure swing adsorption in principle allows these complex measures to be eschewed.

In one embodiment of the present invention, in particular of the previously elucidated first embodiment, when using such low temperatures the low-temperature rectification may be performed using a liquid reflux which is formed by condensation of a part of the gaseous first fraction which in this case contains methane. In this way the content of ethane and ethylene in the gaseous first fraction may be reduced.

As a result of the pressure swing adsorption ethylene can be recovered and expanders which would otherwise be installed for production of peak refrigeration from the gaseous first fraction in order also to be able to recover final residues of ethane and ethylene may be dispensed with. The gaseous first fraction may be utilized for heat integration in this case too and the ethylene-free residual gas stream, i.e. the fourth fraction containing predominantly or exclusively compounds having a lower boiling point than ethane and ethylene from the pressure swing adsorption, may for example be sent for thermal recovery or otherwise utilized. As mentioned, due to the small amounts of ethane and ethylene in the gaseous first fraction the pressure swing adsorption may in principle be made substantially smaller in this embodiment than in an embodiment in which higher temperature levels are used.

If higher temperature levels are employed in the low-temperature separation for separating the condensate(s) these are advantageously not less than −20° C. to −40° C., in particular −30° C. to −40° C., for example −35° C. to −40° C. The condensates are thus separated at temperature levels not lower than the recited values. This does not exclude the possibility that the condensates themselves may subsequently be supplied to further cooling steps, as is the case for example in the second embodiment illustrated in FIG. 3 for example. These temperature levels may also be achieved through the use of C3 refrigerant, i.e. in particular propylene. On account of the markedly higher temperatures than elucidated above, both apparatus and material requirements are reduced. However the amounts of ethane and ethylene which may then be transferred into the gaseous first fraction in larger amounts may need to be removed in a correspondingly larger pressure swing adsorption. The respective advantages of the lower or higher temperature levels must be weighed up according to the circumstances at hand, for example the presence of a (C2 or C3) refrigeration circuit.

When using higher temperature levels to separate the condensates as elucidated hereinabove the separation input may be compressed to a pressure level of 25 to 35 bar, for example about 30 bar, before the cooling in the second embodiment of the present invention. The low-temperature rectification may then be performed at a pressure level of 15 to 25 bar, for example about 19 bar, at which the low-temperature rectification is also operated. The condensate(s)

subjected to the low-temperature rectification, or the part thereof subjected to the low-temperature rectification, is/are then decompressed to the pressure level of the low-temperature rectification before being supplied to the low-temperature rectification.

When using higher temperature levels to separate the condensates as elucidated hereinabove the separation input may, as an alternative to the just now elucidated second embodiment, be compressed to a pressure level of 20 to 25 bar, for example about 22 bar, before the cooling in the third embodiment of the present invention. The low-temperature rectification may then be operated at a pressure level 9 to 16 bar, in particular about 13 bar. The condensate(s) subjected to the low-temperature rectification, or the part thereof subjected to the low-temperature rectification, is/are here too decompressed to the pressure level of the low-temperature rectification before being supplied to the low-temperature rectification. It is thus possible to obtain a biphasic mixture which is separated into a gas phase and a liquid phase. The gas phase and the liquid phase may each be at least partly supplied to the low-temperature rectification and for example introduced into a rectification column at different heights. The decompression can generate additional refrigeration.

When using the elucidated comparatively higher pressures an adequate low-temperature rectification is possible at comparatively higher temperatures and the condensate(s) therefore require cooling to a lesser extent. Conversely when using the elucidated comparatively lower pressures a lower temperature is required but the plant parts involved may be made in a more cost-effective fashion on account of requiring less pressure resistance. Accordingly in certain scenarios one or other of the embodiments may be advantageous.

In particular in the second and third embodiments in which the comparatively higher temperature levels are employed the residue of the separation input remaining in gaseous form in the condensation or a part thereof may, as mentioned, be supplied to the low-temperature rectification.

Irrespective of the employed pressure level the separation input may be cooled by transferral of heat to the liquid second fraction in the second and third embodiments of the present invention. The cooling of the separation input thus comprises in particular transferral of heat to the second fraction.

The cooling of the separation input to the mentioned higher temperature level to separate the condensates may further comprise the use of suitable refrigerants. Suitable in particular is a C3 refrigerant such as propylene, which allows the temperature level of −20° C. to −40° C. to be achieved.

As mentioned, the condensates in the embodiments elucidated here may be further cooled, in particular before decompression. Different temperature levels may be employed depending on the above-described pressure levels. Thus, in the case of the elucidated higher pressure level of the separation input and of the rectification according to the second embodiment the condensate(s) or the part thereof subjected to the low-temperature rectification may be further cooled to a temperature level of −30° C. to −50° C. by transferral of heat to the first fraction. By contrast, in the case of the elucidated lower pressure levels according to the third embodiment the condensate(s) or the part thereof subjected to the low-temperature rectification may be further cooled to a temperature level of −90° C. to −100° C. by transferral of heat to the first fraction and a refrigerant.

Advantageously the gaseous first fraction is used for cooling the condensate(s) or the respective parts thereof by also employing a further refrigerant, in particular a C2 refrigerant such as ethylene, especially when the recited low temperatures are to be achieved. The gaseous first fraction may in particular be decompressed before its use for cooling the condensate(s) or the parts thereof and supplied to the pressure swing adsorption after its use for cooling.

The invention also extends to a plant for producing ethylene which is adapted for using a dehydrogenation of ethane to form a process gas containing at least ethane, ethylene and compounds having a lower boiling point than ethane and ethylene and using at least a part of the process gas to form a separation input and subjecting said input to a low-temperature separation and which provides means adapted for cooling the separation input, separating one or more condensates from the separation input and at least partly subjecting the condensate(s) to a low-temperature rectification to obtain a gaseous first fraction and a liquid second fraction, wherein the low-temperature rectification is adapted for forming the gaseous first fraction such that it contains at least the ethane and the ethylene in a lower proportion than in the separation input and the compounds having a lower boiling point than ethane and ethylene in a higher proportion than in the separation input.

Provided according to the invention are means adapted for at least partly subjecting the gaseous first fraction to a pressure swing adsorption and by means thereof forming a third fraction containing predominantly or exclusively ethane and ethylene and a fourth fraction containing predominantly or exclusively the compounds having a lower boiling point than ethane and ethylene.

For features and advantages of a corresponding plant, reference is made to the above elucidations concerning the features and advantages of the process. In particular such a plant is adapted for performing a process according to the specific embodiments elucidated above and comprises means suitable therefor. In this regard too, reference is made to the above intimations.

BRIEF DESCRIPTION OF THE DRAWINGS

The invention is more particularly elucidated below with reference to the appended drawings which illustrate inter alia preferred embodiments of the present invention.

DETAILED DESCRIPTION OF THE DRAWINGS

In the figures that follow, functionally or structurally equivalent elements are indicated with identical reference numerals and for the sake of simplicity are not repeatedly elucidated. When plants and plant parts are described hereinbelow the elucidations concerning these also apply correspondingly to the process steps implemented by means of these plant parts and vice versa.

Figure 1:
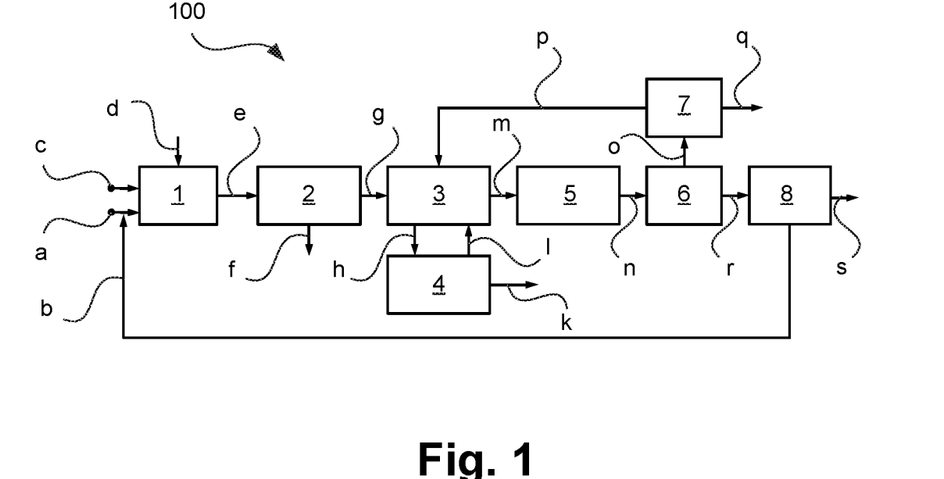
FIG. 1 shows a plant for producing olefins according to one embodiment of the invention.

In FIG. 1 a plant for producing olefins according to one embodiment of the invention in the form of a greatly simplified plant diagram is illustrated and collectively referred to as 100. Notwithstanding that a plant 100 for ODH of ethane (ODH-E) is described below, the present invention is also suitable, as mentioned, for use in a non-oxidative dehydrogenation of ethane. In this case the elucidations which follow apply correspondingly.

In the plant 100 an ethane-rich fresh input a which may contain small amounts of methane is mixed with an ethane-rich, recycled material stream b and supplied to one or more ODH-E reactors 1. The reactor(s) is/are further supplied with a diluent c (for example steam, nitrogen or carbon dioxide) and oxygen d.

The principal reaction of ODH-E is:

$$C_2H_8 + \tfrac{1}{2}O_2 \rightarrow C_2H_4 + H_2O \quad (1)$$

Side reactions that occur are especially the formation of carbon monoxide, carbon dioxide and also of acetic acid.

A gas mixture withdrawn from the reactor(s) 1 in the form of a material stream e, referred to here as "process gas", is subjected to a cooling 2 and water is removed in the form of a material stream F. Any acetic acid present is likewise removed from the process gas and discharged with the material stream f. The material stream f may subsequently be subjected to further processing to obtain acetic acid (not shown).

The cooled process gas in the form of a material stream g is subjected to a compression 3 and compressed, generally in a multi-stage compressor. Between the compressor stages the process gas is withdrawn in the form of a material stream h to remove carbon dioxide in the form of a material stream k. This may be effected for example by an amine scrub, potash scrub or lye scrub in a carbon dioxide removal unit 4. Also employable are other processes such as membrane processes or a combination of different processes. The process gas freed from carbon dioxide is passed back to the compression 3 in the form of a material stream I.

The compressed process gas is supplied to a drying 5 in the form of a material stream m and the accordingly dried process gas is supplied to a low-temperature separation 6 in the form of a material stream n. Details of a low-temperature separation 6 are illustrated in the form of exemplary embodiments in FIGS. 2, 3 and 4.

In the low-temperature separation 6 the process gas/a separation input formed therefrom is cooled via one or more temperature levels and one or more condensates are separated from the process gas, wherein the condensate(s) is/are at least partly subjected to a low-temperature rectification to obtain a gaseous ("first") fraction and a liquid ("second") fraction, wherein the gaseous first fraction contains at least the ethane and the ethylene in a lower proportion than in the separation input and at least the compounds having a lower boiling point than ethane and ethylene in a higher proportion than in the separation input. The process gas is thus subjected to a staged cooling and condensate generated is supplied to a rectification column.

At the top of the rectification column the mentioned gaseous first fraction is withdrawn in the form of a material stream o. To form the material stream o it is also possible to use a proportion of the process gas remaining in gaseous form in the mentioned staged cooling. Due to the mentioned small amounts of the methane usable as reflux in the low-temperature rectification this material stream o still contains considerable amounts of ethane and ethylene.

To reduce the losses of product (ethylene) and reactant (ethane) a pressure swing adsorption 7 for recovering ethylene (and also ethane) is proposed in the plant 100 shown in FIG. 1. Here ethane and ethylene are adsorbed from the material stream o by a suitable adsorbent. Ethane and ethylene are preferably adsorbed in contrast with the light gases nitrogen and argon which are in particular introduced into the plant 100 as impurities in the oxygen d but also in contrast with oxygen, carbon monoxide, methane and other light gases such as hydrogen.

Ethane and ethylene are discharged again at lower pressure in the form of a ("third") fraction containing predominantly ethane and ethylene and may be discharged in the form of a material stream p. The material stream p may in particular be recycled to the compression 3. The material stream o freed from ethylene and ethane and now labelled q, i.e. a ("fourth") fraction containing predominantly or exclusively components having a lower boiling point than ethane and ethylene, is still under high pressure and can be utilized for obtaining mechanical work and thermal energy or as an export stream for other applications. The material stream o may also be utilized for refrigeration recovery before the adsorption.

The basic idea of the present invention consists in a combination of a low-temperature separation 6 with a pressure swing adsorption 7. Different embodiments may be envisaged here. In one embodiment illustrated in FIG. 2 a cooling of the process gas to an extremely low temperature level is undertaken, so that the content of ethane and ethylene in the material stream o which is subsequently subjected to the pressure swing adsorption is reduced. In further embodiments illustrated in FIGS. 3 and 4 a cooling of the process gas to a markedly higher temperature level is undertaken, so that the content of ethane and ethylene is reduced to a corresponding extent only in the pressure swing adsorption.

Remaining in the low-temperature separation 6 is the liquid second fraction which may be withdrawn from the low-temperature separation 6 in the form of a material stream r. This liquid second fraction contains predominantly or exclusively ethylene and ethane. In the example shown the material stream r is supplied in a splitter 8 which likewise comprises a low-temperature rectification. An ethylene product containing predominantly or exclusively ethylene is obtained in the splitter 8 and withdrawn in the form of a material stream s. A fraction containing predominantly or exclusively ethane likewise formed in the splitter 8 may be recycled to the reactor(s) in the form of the material stream b.

If a heavy fraction of hydrocarbons having three or more carbon atoms exists, said fraction may be removed upstream or downstream of the low-temperature separation 6. Depending on the amount these heavy hydrocarbons may also be removed from the material stream b.

Figure 2:
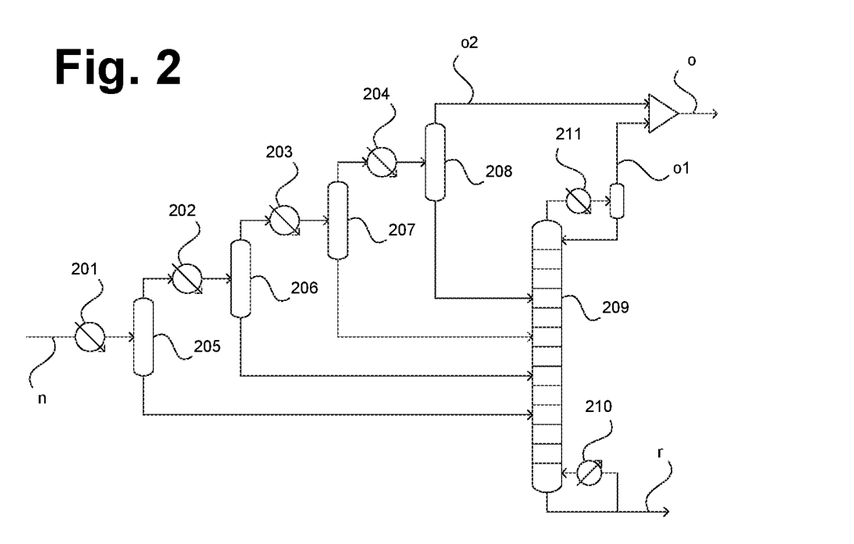
FIG. 2 shows a low-temperature separation for use in a plant according to one embodiment of the invention.

FIG. 2 illustrates a low-temperature separation for use in a plant for producing olefins, such as may be employed for example as a low-temperature separation 6 in the plant 100 shown in FIG. 1. This low-temperature separation which corresponds to the previously elucidated first embodiment comprises a staged cooling. The material streams n, o and r already depicted in FIG. 1 are also shown here to illustrate the integration of the low-temperature separation shown in FIG. 2 into a corresponding plant 100. The depiction of the respective elements is not true to position and not true to scale.

The process gas is supplied to the low-temperature separation in the form of the material stream n. The process gas is successively passed through heat exchangers 201 to 204 and therein cooled to ever lower temperature levels. To this end the heat exchangers 201 to 204 may be cooled with ethylene streams (not shown). Also employable for cooling and likewise not shown separately is the material stream o, i.e. the gaseous first fraction elucidated repeatedly above.

Downstream of the heat exchangers 201 to 204 the process gas/a biphasic mixture formed in each case by cooling in the heat exchangers 201 to 204 is in each case transferred into separators 205 to 208 where in each case a condensate is separated from the process gas. The condensates are introduced into a rectification column 209 at a height corresponding to their composition of matter. A smaller proportion of the process gas of the material stream n may also be introduced directly into the rectification column 209 (not shown here).

A bottoms evaporator 210 of the rectification column 209 is heated using propane for example, a tops condenser 211 is cooled using low-pressure ethylene for example. The rectification column 209 is operated such that predominantly components having a lower boiling point than ethane and ethylene undergo enrichment at its top and the higher boiling compounds undergo enrichment at its bottom. In this way a portion of the material stream o, referred to here as o1, may be withdrawn from the top of the rectification column 209 and the material stream r may be withdrawn from the bottom of the rectification column 7. A proportion of the process gas remaining in gaseous form in the separator 208, illustrated here in the form of a material stream o2, may likewise be used in the formation of the material stream o.

The temperature of the process gas/downstream of the heat exchanger 201 is for example about −30° C., the temperature downstream of the heat exchanger 202 for example about −50° C., the temperature downstream of the heat exchanger 203 for example about −75° C. and the temperature downstream of the heat exchanger 204 for example about −99° C. The bottoms evaporator 210 is operated at a temperature level of for example about −17° C., the tops condenser 211 at a temperature level of for example about −97° C.

Correspondingly low temperatures are achievable by use of an appropriate chiller, for example with the refrigerant ethylene. In this way the proportion of ethylene in the gaseous first fraction, i.e. the material stream o, can be substantially reduced. The use of a pressure swing adsorption 7 for removal of ethylene may nevertheless be energetically and economically advantageous depending on the composition of the process gas/of the material stream n.

In this case the pressure swing adsorption recovers ethane and ethylene and expanders which would otherwise be installed, where required, for the production of peak refrigeration from the material stream o may be dispensed with. The material stream o may continue to be utilized for heat integration and the ethylene-free residual gas stream q (see FIG. 1) may be recovered as in the preceding case. In addition, the pressure swing adsorption may be made substantially smaller than when no cooling to correspondingly low temperature levels is undertaken.

FIG. 3 illustrates a low-temperature separation for use in a plant for producing olefins, such as may likewise be employed for example as a low-temperature separation 6 in the plant 100 shown in FIG. 1. This low-temperature separation which operates with the previously elucidated higher temperature levels comprises a multistage cooling to a markedly higher temperature level than elucidated for FIG. 2. Here too, the material streams n, o and r depicted in FIG. 1 are shown to illustrate the integration of the low-temperature separation shown in FIG. 3 into a corresponding plant 100. Also shown here in addition are the pressure swing adsorption 7 and the material streams p and q.

The process gas is introduced into the low-temperature separation at a temperature level of for example about −9° C. and at a pressure level of for example about 30 bar and passed through a first heat exchanger 301 which may be cooled using the material stream r, i.e. the liquid second fraction. After cooling in the first heat exchanger 301 the process gas is then cooled to a temperature level of for example about −35° C. in a second heat exchanger 306. Formed in this way is a biphasic stream which is introduced into a separation vessel 302. A liquid fraction and a gaseous faction are formed in the separation vessel 302. The gaseous fraction is decompressed and introduced into a rectification column 305. The decompression into the second separation vessel 304 is effected from the pressure level of for example about 30 bar to a pressure level of for example about 19 bar at which the rectification column 305 is also operated. The heat exchanger 306 may be operated for example with low-pressure propylene or a corresponding C3 refrigerant.

The liquid fraction is withdrawn from the first separation vessel 302 and cooled in a third heat exchanger 303 to a temperature level of for example about −38° C. and decompressed into a second separation vessel 304 to the pressure level at which the rectification column is operated. This forms a liquid fraction and a gaseous fraction which are introduced into the rectification column. The liquid fraction is used as reflux onto the rectification column 305. The gaseous fraction from the first separation vessel 302 is also introduced into the rectification column.

The rectification column 305 is operated using a bottoms evaporator which may be operated with low-pressure propylene for example. The material stream r may be withdrawn from the rectification column 305 at a temperature level of for example about −21° C. From the top of the rectification column 305 the material stream o is withdrawn at a temperature level of for example about −45° C., decompressed further and passed through the second heat exchanger 303.

The material stream o, i.e. the gaseous second fraction, is subsequently introduced into the pressure swing adsorption 7. For details of this and the further treatment of the material streams p and q reference is made to the elucidations in respect of FIG. 1.

FIG. 4 illustrates a low-temperature separation for use in a plant for producing olefins, such as may likewise be employed for example as a low-temperature separation 6 in the plant 100 shown in FIG. 1. This low-temperature separation constitutes a variant of the low-temperature separation illustrated in FIG. 3 which differs essentially in terms of the pressures and temperatures used. The elements shown are therefore labelled with identical reference numerals.

Here too a cooling to the elucidated comparatively high temperature levels is effected in the heat exchangers 301 and 306. However, the separation input for the low-temperature separation is supplied at for example about 22 bar and the low-temperature rectification is performed at for example about 13 bar. The liquid fraction withdrawn from the first separation vessel 302 is here cooled to a temperature level of for example about 97° C. in the third heat exchanger 303 by additional use of a suitable coolant in the form of a material stream. In this way the material stream r may be withdrawn from the rectification column 305 at a temperature level of for example about −35° C. From the top of the rectification column 305 the material stream o is withdrawn at a temperature level of for example about −97° C., decompressed further and passed through the second heat exchanger 303.

The invention claimed is:

1. A process for producing ethylene wherein using a dehydrogenation of ethane a process gas containing at least ethane, ethylene and compounds having a lower boiling point than ethane and ethylene is formed, wherein using at least a part of the process gas a separation input is formed and subjected to a low-temperature separation (6) in which the separation input is cooled and in which one or more condensates are separated from the separation input and wherein at least a part of the condensate(s) are subjected to a low-temperature rectification column to obtain a gaseous first fraction and a liquid second fraction, wherein the gaseous first fraction contains at least the ethane and the ethylene in a lower proportion than in the separation input and the compounds having a lower boiling point than ethane and ethylene in a higher proportion than in the separation input, characterized in that the gaseous first fraction is at least partly subjected to a pressure swing adsorption (7) by means of which a third fraction containing predominantly or exclusively ethylene and ethane and a fourth fraction containing predominantly or exclusively methane and carbon monoxide are formed.

2. The process according to claim 1, wherein in the low-temperature separation (6) for separating the condensate(s) the separation input is cooled to a temperature level of −40° C. to −100° C.

3. The process according to claim 2, wherein the low-temperature rectification is performed using a liquid reflux which is formed by condensing a part of the gaseous first fraction.

4. The process according to claim 1, wherein in the low-temperature separation (6) for separating the condensate(s) the separation input is cooled to a temperature level of −20° C. to −40° C.

5. The process according to claim 4, wherein the separation input is compressed to a pressure level of 25 to 35 bar before the cooling and the low-temperature rectification is operated at a pressure level of 15 to 25 bar.

6. The process according to claim 4, wherein the separation input is compressed to a pressure level of 20 to 25 bar before the cooling and the low-temperature rectification is operated at a pressure level of 9 to 16 bar.

7. The process according to claim 4, wherein the cooling of the separation input comprises transfer of heat to the liquid second fraction.

8. The process according to claim 7, wherein the cooling of the separation input comprises transfer of heat to a refrigerant.

9. The process according to claim 5, wherein the condensate(s) or the part thereof subjected to the low-temperature rectification is or are further cooled to a temperature level of −30° C. to −30° C. by transfer of heat to the gaseous first fraction.

10. The process according to claim 6, wherein the condensate(s) or the part thereof subjected to the low-temperature rectification is or are cooled to a temperature level of −40° C. to −100° C. by transfer of heat to the gaseous first fraction and a refrigerant.

11. The process according to claim 9, wherein the gaseous first fraction is decompressed before heat from the condensate(s) or the part thereof subjected to the low-temperature rectification is transferred thereto.

12. The process according to claim 11, wherein after the transfer of the heat the gaseous first fraction is supplied to the pressure swing adsorption (7).

13. The process according to claim 4, wherein a proportion of the separation input which remains gaseous during the formation of the condensates is also at least partly supplied to the low-temperature rectification.

* * * * *